(12) United States Patent
Zegdi

(10) Patent No.: US 8,246,675 B2
(45) Date of Patent: Aug. 21, 2012

(54) KIT FOR IMPLANTING IN A DUCT

(75) Inventor: Rachid Zegdi, Clamart (FR)

(73) Assignee: Laboratoires Perouse, Ivry le Temple (FR)

( * ) Notice: Subject to any disclaimer, the term of this patent is extended or adjusted under 35 U.S.C. 154(b) by 477 days.

(21) Appl. No.: 10/583,658

(22) PCT Filed: Dec. 23, 2003

(86) PCT No.: PCT/FR03/03880
§ 371 (c)(1),
(2), (4) Date: Mar. 12, 2007

(87) PCT Pub. No.: WO2005/070343
PCT Pub. Date: Aug. 4, 2005

(65) Prior Publication Data
US 2007/0198097 A1    Aug. 23, 2007

(51) Int. Cl.
*A61F 2/24* (2006.01)
(52) U.S. Cl. ................... 623/1.24; 623/2.18
(58) Field of Classification Search ........ 623/1.24–1.26, 623/2.1–2.19, 900; 606/106, 198, 200
See application file for complete search history.

(56) References Cited

U.S. PATENT DOCUMENTS

| | | | |
|---|---|---|---|
| 4,339,831 A | | 7/1982 | Johnson |
| 4,731,075 A * | | 3/1988 | Gallo Mezo et al. ........ 623/2.17 |
| 6,371,983 B1 * | | 4/2002 | Lane ........................... 623/2.14 |
| 6,425,916 B1 * | | 7/2002 | Garrison et al. ............. 623/2.11 |
| 6,482,228 B1 * | | 11/2002 | Norred ........................ 623/2.17 |
| 6,530,952 B2 * | | 3/2003 | Vesely .......................... 623/2.18 |
| 6,939,365 B1 * | | 9/2005 | Fogarty et al. ............... 606/227 |
| 7,252,681 B2 * | | 8/2007 | Berg et al. .................... 623/2.14 |
| 2001/0007956 A1 * | | 7/2001 | Letac et al. .................. 623/2.11 |
| 2002/0032481 A1 * | | 3/2002 | Gabbay ........................ 623/2.11 |
| 2002/0123802 A1 | | 9/2002 | Snyders |
| 2002/0143387 A1 * | | 10/2002 | Soetikno et al. ............. 623/1.15 |
| 2002/0188344 A1 * | | 12/2002 | Bolea et al. .................. 623/1.11 |
| 2003/0014104 A1 | | 1/2003 | Cribier |
| 2003/0040792 A1 | | 2/2003 | Gabbay |
| 2003/0055492 A1 * | | 3/2003 | Shaolian et al. ............. 623/1.24 |
| 2003/0109924 A1 | | 6/2003 | Cribier |
| 2003/0149477 A1 | | 8/2003 | Gabbay |
| 2004/0210307 A1 * | | 10/2004 | Khairkhahan ................ 623/2.18 |
| 2005/0096735 A1 * | | 5/2005 | Hojeibane et al. ........... 623/1.24 |
| 2006/0212110 A1 * | | 9/2006 | Osborne et al. .............. 623/1.24 |
| 2007/0016286 A1 * | | 1/2007 | Herrmann et al. ........... 623/2.11 |

FOREIGN PATENT DOCUMENTS

| | | |
|---|---|---|
| DE | 42 34 127 | 5/1994 |
| EP | 0 850 607 A | 7/1998 |
| WO | 01/28459 | 4/2001 |
| WO | 02/22054 A | 3/2002 |

* cited by examiner

*Primary Examiner* — Brian Pellegrino
*Assistant Examiner* — Cheryl Miller
(74) *Attorney, Agent, or Firm* — Wenderoth, Lind & Ponack, L.L.P.

(57) ABSTRACT

A kit for implanting in a duct, which includes a tubular endoprosthesis and a prosthetic valve is disclosed. The prosthetic valve includes a carrier frame that is radially deformable in elastic manner relative to a central axis of the tubular endoprosthesis between a deployed, implanted position, and a folded, implanting position. The carrier frame is urged elastically towards its deployed position. A flexible shutter is connected to the carrier frame. The shutter is deformable between an obstruction position in which it is extended transversely, and a release position in which it is contracted transversely under to allow a fluid to flow through the carrier frame. The carrier frame also includes an integrated centripetal compressing mechanism for centripetally compressing the carrier frame towards folded position.

13 Claims, 5 Drawing Sheets

KIT FOR IMPLANTING IN A DUCT

BACKGROUND OF THE INVENTION

1. Field of the Invention

The present invention relates to a kit for implanting in a duct, the kit being of the type comprising:
- a tubular endoprosthesis; and
- a prosthetic valve.

The heart comprises two atria and two ventricles which are separated by valves. Valves are also present at the outlet from the right ventricle (pulmonary valve) and from the left ventricle (aortic valve).

These valves ensure that blood flows in one direction only, preventing a backflow of blood at the end of ventricular contraction.

Valves can suffer from diseases. In particular, they can suffer from poor opening, thereby reducing blood flow, or from not being fully leaktight, thus allowing backflow or regurgitation towards the ventricle that expels the blood flow.

These problems of regurgitation lead to abnormal dilation of the ventricle which can lead in the long run to heart failure.

2. Description of the Related Art

It is known to treat this type of disease surgically, by replacing the diseased valve. Diseased valves, and in particular the pulmonary valve at the outlet from the right ventricle, are replaced by a valve taken from a deceased donor, or by a bioprosthesis constituted by a metal frame and a shutter made of a tissue of animal origin. The shutter is permanently secured to the frame.

Prosthetic valves are also known. These are constituted by a metal frame supporting a polymer shutter. Such valves are described in particular in documents WO 01/154625 and WO 01/28459.

In such prostheses, the frame is elastically deformable to a small extent only, and the shutter is constituted by a pouch. The elastically deformable frame bears against the inside wall of an organic duct, in particular the pulmonary artery coming from the right ventricle.

It has been found that, after such a prosthesis has been implanted for several years, it degrades and no longer operates effectively. It is then necessary to put a new prosthesis into place.

However, it is not possible to withdraw the old prosthesis in an endoluminar manner, in particular because the carrier frame of the prosthesis has become secured to the heart wall, meaning that they cannot be separated without major surgical intervention for replacing the valve.

SUMMARY OF THE INVENTION

An object of the invention is to propose a kit comprising a prosthetic valve that can be replaced without excessive difficulty, and without requiring major surgical intervention.

To this end, the invention provides a kit of the type specified, in which the prosthetic valve is for implanting removably in the tubular endoprosthesis. The prosthetic valve comprises: firstly, a carrier frame that is radially deformable in elastic manner relative to a main axis between a deployed implanted position and a folded, implanting position, which carrier frame is urged resiliently towards its deployed position; and secondly, a flexible shutter connected to the carrier frame and deformable between an obstruction position in which it is extended transversely, and a release position in which it is contracted transversely under the action of the flow passing through the carrier frame; and an integrated centripetal compression means for compressing the carrier frame towards its folded position against the elastic action.

In particular embodiments, the kit includes one or more of the following characteristics:
- the shutter comprises a pouch;
- the pouch includes an evacuation orifice formed in its end wall;
- the end wall of the kit is generally hemispherical;
- the centripetal compression means comprises a clamp having at least two branches connected together in a common region, each branch being connected to the shutter by a connection segment, each of the branches presenting a drive segment suitable for co-operating with a complementary clamping member for centripetally compressing the carrier frame towards its folded position;
- the branches are welded together in their common region, and the carrier frame is fork-shaped, each branch being elastically deformable, the drive segments and the connection segments for connecting the branches to the shutter both being situated on the same side of the weld;
- the carrier frame has two branches;
- the carrier frame has three branches;
- the valve includes threads connecting the end wall of the pouch to each of the branches; and
- the carrier frame comprises a resilient wire mesh and the centripetal compression means comprises a constriction strand engaged around the resilient wire mesh.

The invention also provides an implanted prosthesis made from a kit as defined above, the endoprosthesis being placed against the inside surface of a duct, and the prosthetic valve being placed in tubular endoprosthesis.

BRIEF DESCRIPTION OF THE DRAWINGS

The invention can be better understood from the following description given purely by way of example and made with reference to the drawings, in which.

DETAILED DESCRIPTION OF THE INVENTION prosthesis of the invention that is adapted to be implanted in a pulmonary artery 12 connected at its end 12A to the outlet from the right ventricle of the heart, in particular of a human being, and at its end 12B to the lungs.

Figure 1:
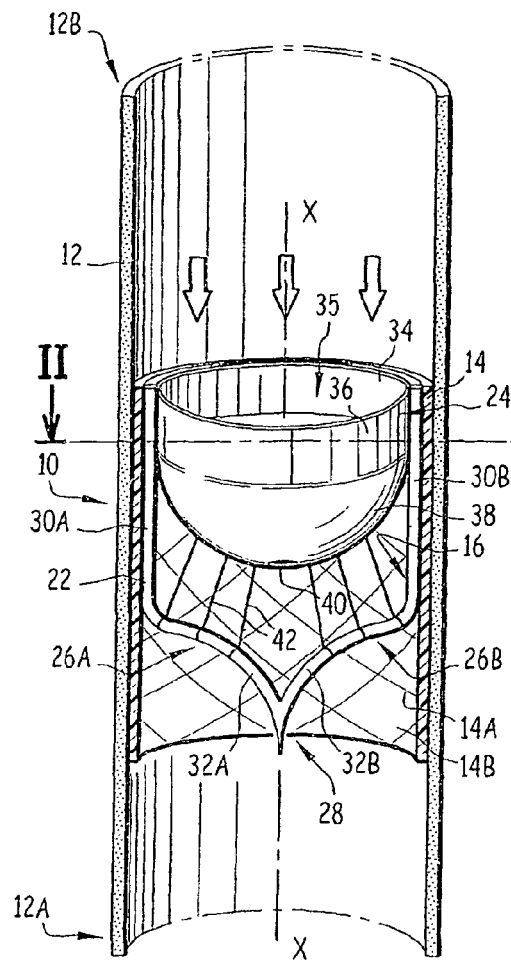
FIG. 1 is a longitudinal section view of a prosthesis implanted in an organic duct, comprising a prosthetic valve in its closed state.

FIG. 1 shows a prosthesis of the invention that is adapted to be implanted in a pulmonary artery 12 connected at its end 12A to the outlet from the right ventricle of the heart, in particular of a human being, and at its end 12B to the lungs.

In the invention, the prosthesis comprises an outer tubular endoprosthesis 14 having disposed therein a removable and replaceable prosthetic valve 16.

By way of example, the endoprosthesis 14 is constituted by a tubular mesh 14A embedded in a stretchable film 14B that is liquid-proof, such as an elastomer. The mesh 14A is made of stainless steel wire having spring properties, such that the endoprosthesis 14 is self-expanding. Such an endoprosthesis is commonly referred to as a "stent".

The endoprosthesis 14 is capable of deforming spontaneously from a compressed state in which it has a small diameter, to a dilated state in which it has a larger diameter, the dilated state constituting its rest state.

In its implanted state, as shown in the figures, and because of its own elasticity, the endoprosthesis 14 bears against the inside surface of the duct 12, thus forming an inside sheath for the duct.

An interchangeable prosthetic valve 16 comprises a carrier frame 22 and a deformable shutter 24 supported by the frame 22 and secured thereto. The valve is generally symmetrical about the axis X-X.

The carrier frame has means integrated therein to compress it centripetally. More precisely, the frame 22 is constituted by two branches 26A, 26B connected together at a first end 28 so as to form a clamp that is elastically deformable between a deployed position in which the two branches are spaced apart from the middle (central) axis X-X, and a folded position in which the two branches are moved towards the middle axis X-X.

The two branches 26A, 26B are generally symmetrical about the middle axis X-X that coincides with the axis of the duct once the prosthesis has been implanted.

The length of the branches measured along the axis X-X lies in the range 2 centimeters (cm) to 4 cm, and is preferably equal to 3 cm.

Each branch 26A, 26B has a bearing segment 30A, 30B for bearing against the endoprosthesis 14. Each bearing segment is constituted by a rectilinear segment extending generally along a generator line of the endoprosthesis 14 when the frame is deployed.

The length of the bearing segments lies in the range 1 cm to 3 cm, and is preferably about 2 cm.

The bearing segments 30A, 30B are extended by drive segments 32A, 32B that converge towards each other onto the connection point 28. These segments are generally inclined relative to the middle axis X-X.

The drive segments 32A, 32B are generally curved and present a center of curvature lying outside the space defined between the two branches. Thus, the segments 32A and 32B bulge towards the inside of the clamp.

The shutter 24 is constituted by a flexible pouch 34 having a generally circular opening 35 on the axis X-X when the pouch is inflated.

The pouch 34 has a generally cylindrical skirt 36 extended by a generally hemispherical end wall 38. The end wall 38 has an orifice 40 of a diameter that is small relative to the section of the opening 35.

By way of example, the pouch 34 is made of polyurethane or out of a biological material (bovine pericardium).

By way of example, the height of the skirt 36 is equal to 4 millimeters (mm) or 5 mm, and it preferably lies in the range 2 mm to 5 mm.

The pouch 34 is connected to the two bearing segments 30A, 30B by adhesive or by any other appropriate means along the length of the generator lines of the skirt 36.

Advantageously, the pouch 34 is connected to the two branches 26A, 26B in such a manner that the two half-skirts defined on either side are of lengths that are slightly different.

Finally, the end wall 38 is connected by threads 42 to the drive segments 32A, 32B of the two branches of the carrier frame so as to prevent the pouch from being turned inside out by invagination.

Figure 2:
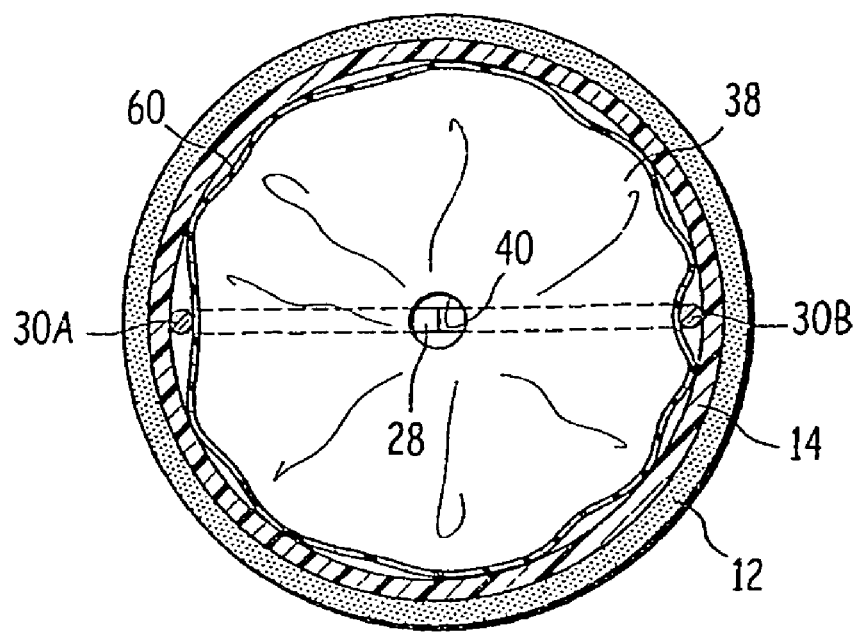
FIG. 2 is a cross-section of the prosthesis illustrated in FIG. 1 along on line II-II.

When implanted, such a prosthetic valve operates as follows. At the end of expulsion from the right ventricle, when the ventricle increases in volume, the blood flow is sucked into the duct 12 from the end 12B towards the end 12A. The blood then fills the pouch 34 which presses against the endoprosthesis 14, as shown in FIGS. 1 and 2, thereby closing off the organic duct 12 in a substantially leaktight manner.

During circulation of the blood, the orifice 40 allows a constant small flow of blood to pass through the pouch 34, thus preventing a blood clot from forming at the bottom of the pouch 34 as a result of possible stagnation of the blood.

Figure 3:
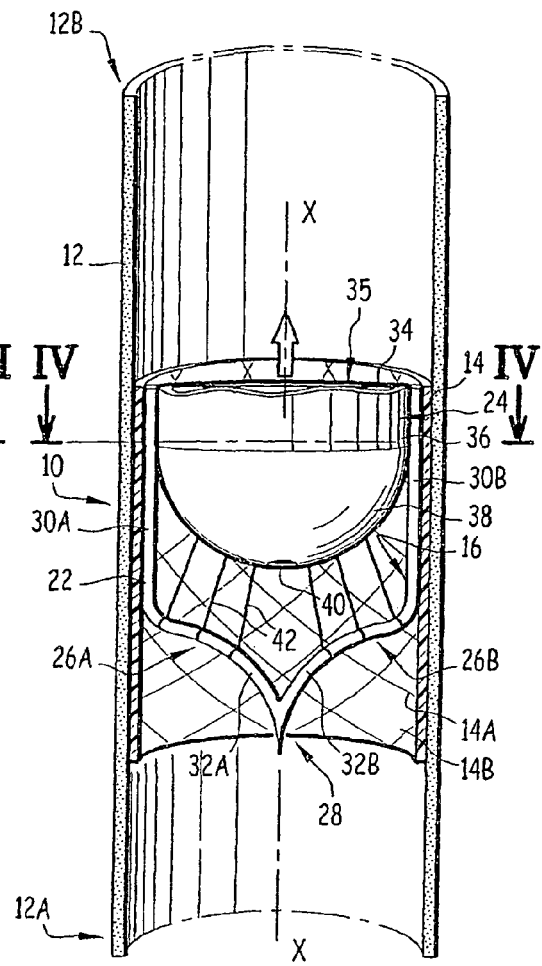
FIGS. 3 and 4 are views identical to FIGS. 1 and 2, with the prosthetic valve being in its open state.
Figure 4:
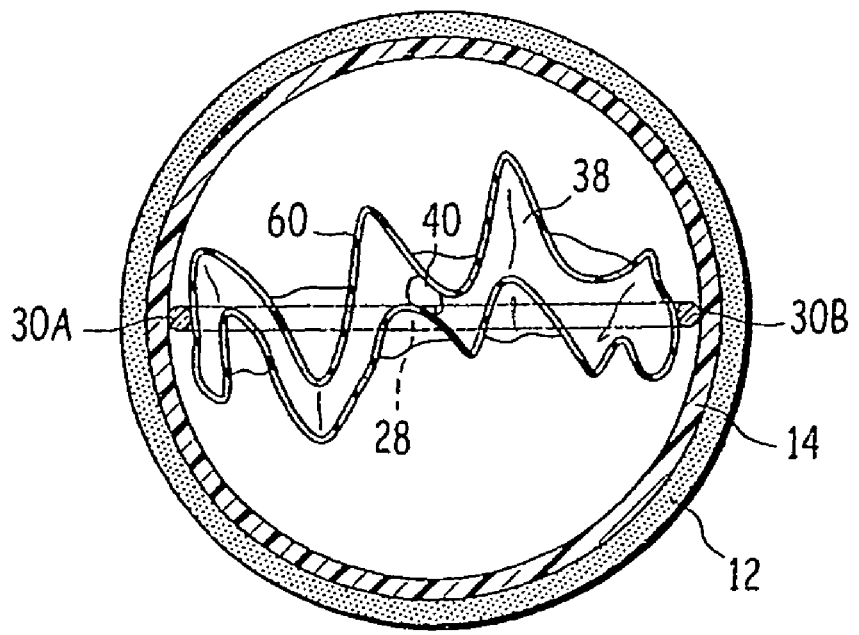

In contrast, during contraction of the right ventricle, blood flows from the end 12A towards the end 12B. As shown in FIGS. 3 and 4, the pouch 34 is urged outwards from its end wall 38, thereby causing the pouch to flatten. The blood is thus free to flow along the duct on either side of the pouch.

The difference in length between the two portions of the skirt disposed on either side of the two arms ensures that in the position shown in FIGS. 3 and 4, the two half-skirts do not press against each other and do not become pressed together definitively against the endoprosthesis 14.

In order to implant the prosthesis in the duct 12, a kit of the invention comprising the endoprosthesis 14 and the prosthetic valve 16 is used.

Initially, the endoprosthesis 14 is implanted in the duct 12 by an endoluminal technique.

Thereafter, the valve 16 is implanted by the endoluminal technique inside the endoprosthesis 14.

After such a prosthesis has been implanted, the wall of the organic duct bonds progressively with the endoprosthesis 14. However, the endoprosthesis 14 constitutes a sheath which acts as a screen between the prosthetic valve 16 and the wall of the duct 12, thus avoiding agglomeration of the organic duct and the prosthetic valve. This means that it is possible to withdraw the prosthetic valve.

In particular, since the prosthetic valve is fitted with centripetal compression means, it can be returned to its compressed state and removed in transluminal manner.

Figure 5:
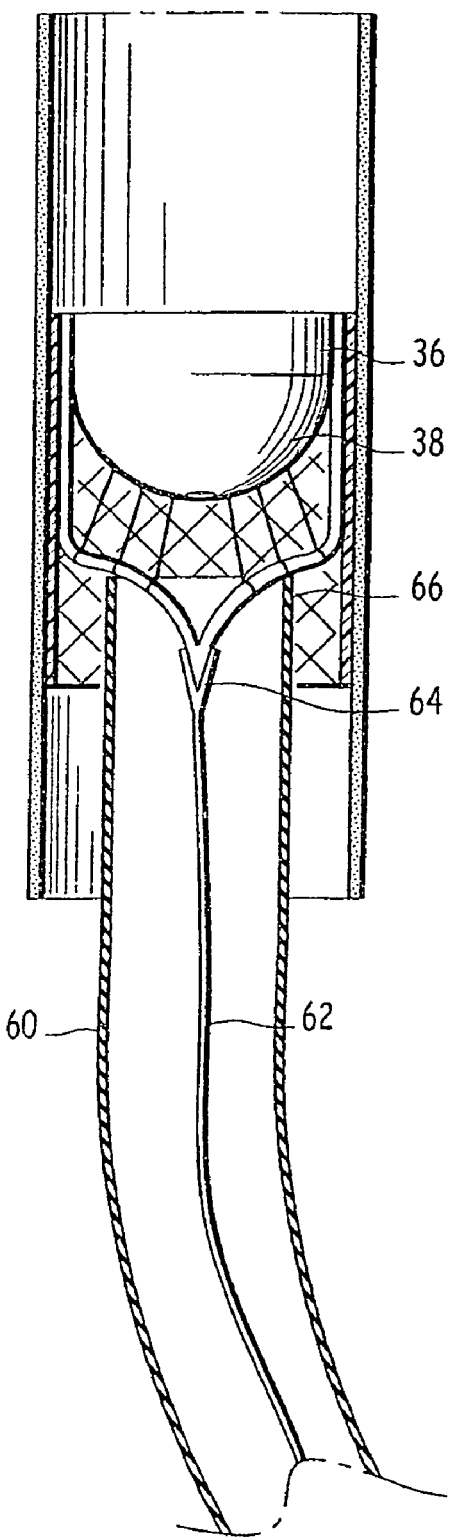
FIGS. 5 and 6 are views identical to that of FIG. 1 showing successive stages in withdrawing a prosthetic valve of the invention.

More precisely, and as shown in FIG. 5, in order to withdraw the prosthetic valve, a catheter 60 is inserted via the right atrium and the right ventricle and is placed in register with the end 28 of the clamp-forming carrier frame.

Figure 6:
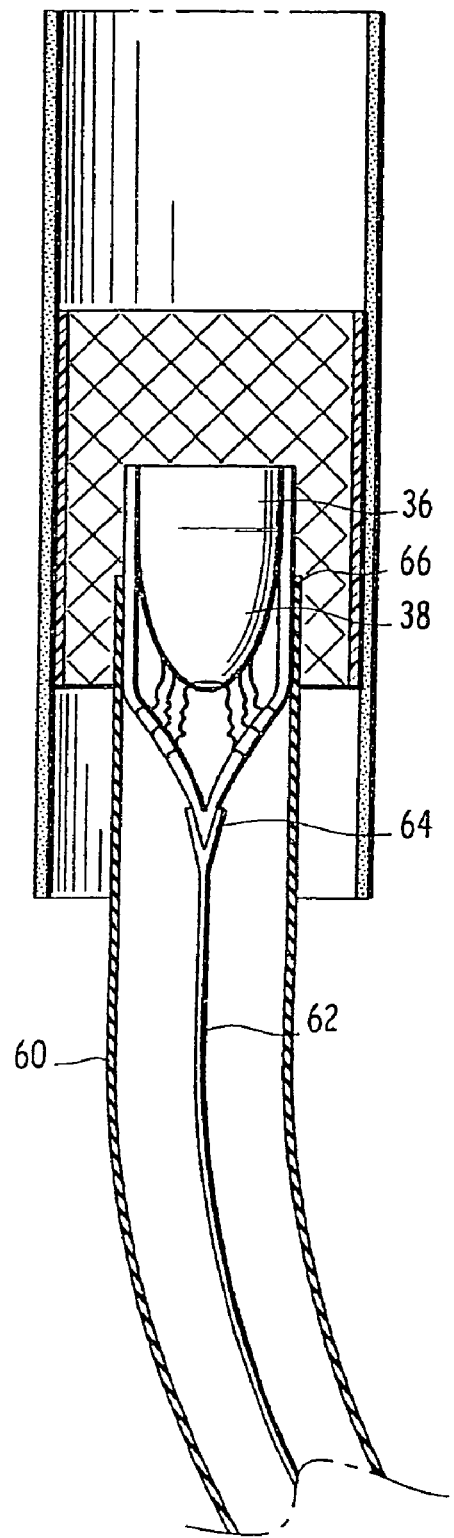

A traction tool 62 is conveyed along the catheter 60. At its end, the tool has a jaw 64 suitable for taking hold of the end 28 of the clamp. When the open end, referenced 66, of the catheter comes into contact with the drive segments 32A, 32B, the carrier frame is pulled progressively into the duct 60. By a camming effect, the two arms 26A, 26B are moved towards each other and the prosthetic valve is brought progressively into its compact state and is inserted into the catheter 60, as shown in FIG. 6. The catheter 60 containing the prosthetic valve is then extracted from the human body.

A new catheter containing a new prosthetic valve is then inserted into the human body and the valve is released by performing the above-described operations in reverse order. In particular, the prosthetic valve is extracted progressively from the catheter 60 by being pushed from its end 28. Under the resilient action of the clamp constituted by the carrier frame 22, the prosthetic valve is deployed and bears radially against the tubular endoprosthesis 14.

Figure 7:
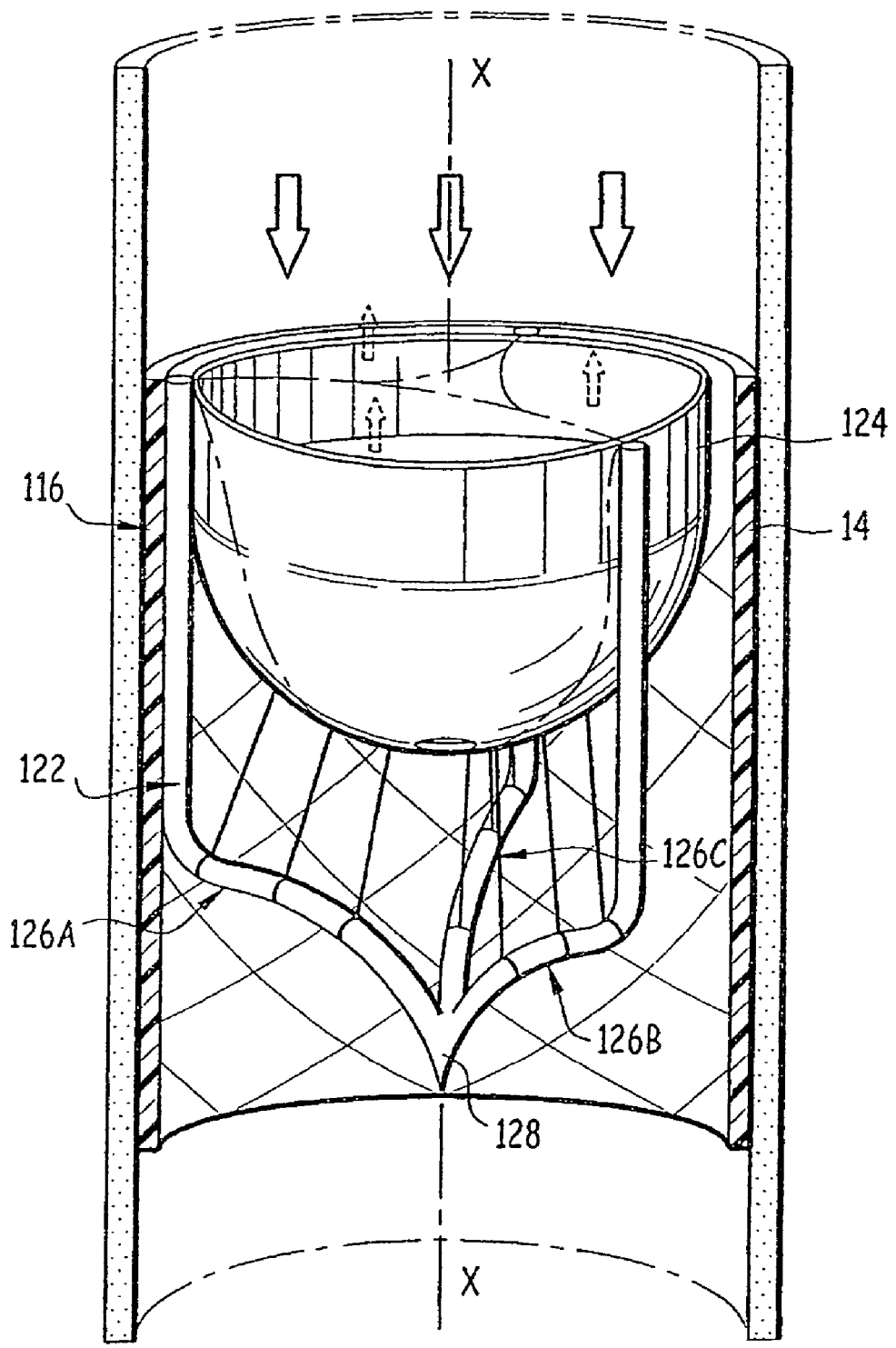
FIG. 7 is a view identical to that of FIG. 1 showing a variant embodiment of a prosthetic valve of the invention.

FIG. 7 shows a variant embodiment of the prosthetic valve of the invention.

In this embodiment, the carrier frame, referenced 122, is constituted by a clamp comprising three arms 126A, 126B, 126C, each in the form of an arm 26A, 26B. These arms are regularly distributed around the longitudinal axis X-X of the prosthesis.

As before, these arms are suitable for bearing against the endoprosthesis 14, and they are connected together at a connection end 128.

Figure 8:
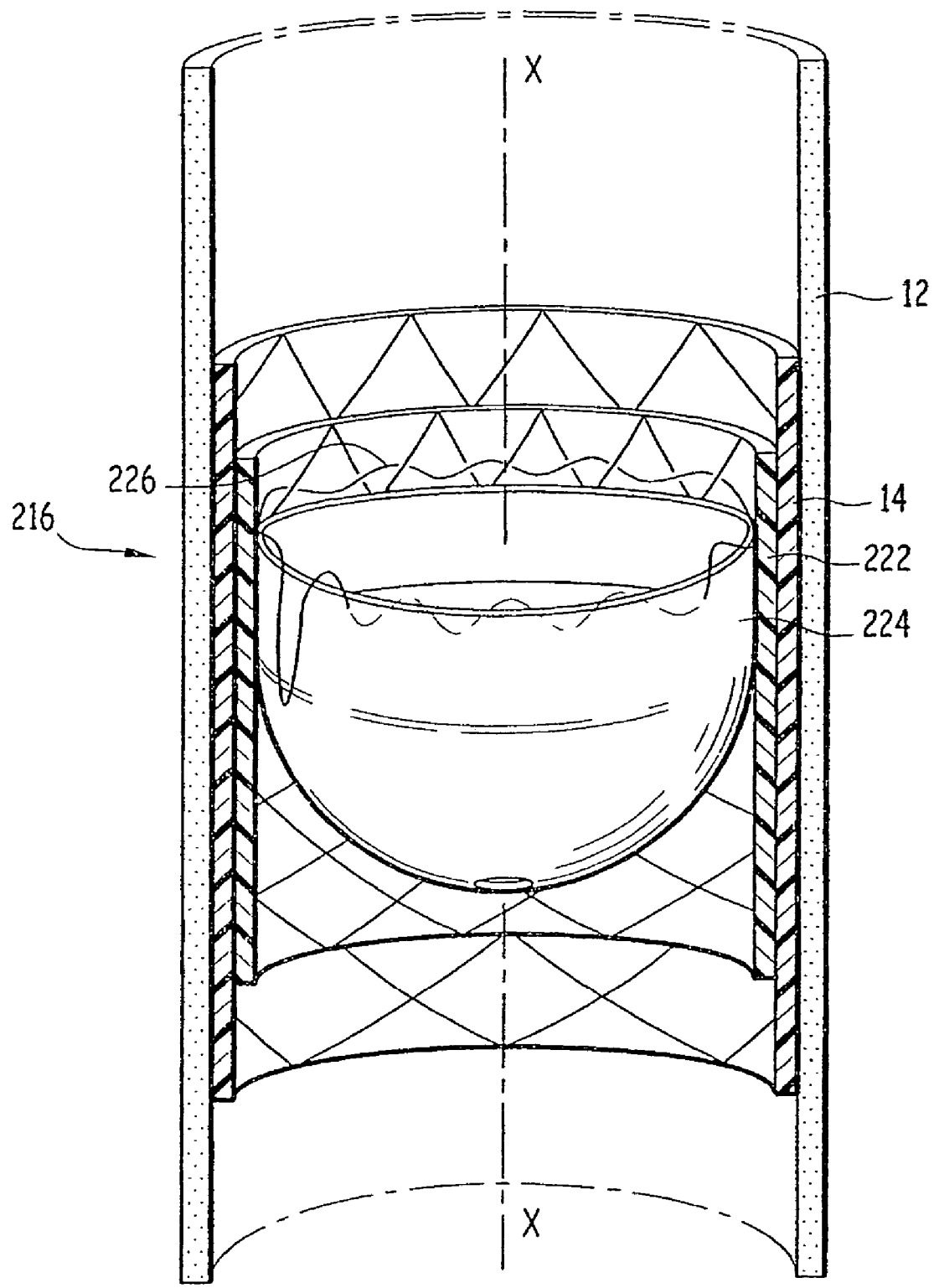
FIG. 8 is a view identical to that of FIG. 1 showing another embodiment of a prosthesis comprising a prosthetic valve.

In yet another variant, as shown in FIG. 8, the prosthetic valve 216 comprises a resilient tubular wire mesh 222 and a shutter-forming pouch 224 identical to the pouch 34. The pouch 224 is connected around its open periphery to the tubular mesh at two or three points.

The prosthetic valve also includes a constriction strand 226 permanently engaged in the various loops defined by the endoprosthesis 216 and extending around its circumference. This strand forms a closed loop. It is long enough to allow the valve to expand. This strand forms the centripetal compression means. Applying traction to the strand, e.g. by means of a clamp, causes the carrier frame 222 to be constricted, thus enabling the prosthetic valve to be withdrawn after it has been engaged in a catheter.

In another variant, the kit is implanted in a prosthetic duct 12, in particular a flexible tube, which has previously been implanted in an organic duct or used as a replacement therefor.

The endoprosthesis 12 is then placed by the endoluminal technique so as to bear against the inside wall of the flexible tube.

In another variant, the kit comprises an endoprosthesis 12 constituted by a rigid ring. The length of the ring is substantially equal to the length of the bearing segments 30A, 30B of the prosthetic valve 16.

This type of kit is used when replacing internal heart valves, in particular the tricuspid valves and the mitral valves.

In order to implant the kit in the heart, the ring already fitted with the prosthetic valve 16 is implanted initially by the surgical technique in the heart, to replace a defective heart valve.

When the prosthetic valve 16 becomes defective, it can also be replaced by the endoluminal technique, as described above.

The invention claimed is:

1. A kit for implanting in a duct, the kit comprising:
   a tubular endoprosthesis; and
   a prosthetic valve configured to be implanted in, and withdrawn from said tubular endoprosthesis;
   wherein said prosthetic valve comprises:
      a resilient carrier frame that is radially deformable in an elastic manner relative to a central axis of said tubular endoprosthesis between a deployed position in which said resilient carrier frame rests against said tubular endoprosthesis, and a folded position, said resilient carrier frame being biased towards the deployed position by its resiliency;
      a flexible shutter connected to said resilient carrier frame, said flexible shutter being deformable between an obstruction position in which said flexible shutter is extended transverse to the central axis of said tubular endoprosthesis and a release position in which said flexible shutter is contracted transverse to the central axis of said tubular endoprosthesis to allow a fluid to flow through said resilient carrier frame; and
      integrated centripetal compression means for compressing said resilient carrier frame from the deployed position towards the folded position,
   wherein said integrated centripetal compression means comprises a clamp having at least two branches connected together at a common region located along a central axis of said resilient carrier frame in the deployed position, each branch having a connection segment connected to said flexible shutter and a drive segment for centripetally compressing said resilient carrier frame towards the folded position, and
   wherein the common region is located at a distance from said connection segments of said branches, said drive segments are located between said connection segments and the common region, axially apart from said connection segments, and said drive segments are spaced axially away from said flexible shutter.

2. The kit according to claim 1, wherein said flexible shutter comprises a pouch having an end wall.

3. The kit according to claim 2, wherein said pouch includes an evacuation orifice formed in said end wall.

4. The kit according to claim 2, wherein said end wall of said pouch is generally hemispherical.

5. The kit according to claim 1, wherein said resilient carrier frame is fork-shaped, each of said branches is elastically deformable, and said branches are welded together at the common region such that said drive segments and said connection segments are located on a first side of the common region.

6. The kit according to claim 1, wherein said at least two branches of said clamp is two branches.

7. The kit according to claim 1, wherein said at least two branches of said clamp is three branches.

8. The kit according to claim 1, wherein
   said flexible shutter comprises a pouch having an end wall; and
   said prosthetic valve further comprises a plurality of threads respectively connecting each of said branches to said end wall of said pouch.

9. The kit according to claim 1, wherein said tubular endoprosthesis is adapted to be positioned against an inside surface of the duct.

10. A method for implanting a kit according to claim 1 in the duct, the method comprising:
    implanting the tubular endoprosthesis in the duct by an endoluminal technique; and
    removably implanting the prosthetic valve inside the tubular endoprosthesis by the endoluminal technique.

11. The method according to claim 10, further comprising:
    compressing the prosthetic valve to the folded position by the integrated centripetal compression means;
    removing the prosthetic valve from the tubular endoprosthesis in a transluminal manner; and
    implanting a new prosthetic valve in the tubular endoprosthesis by the endoluminal technique.

12. The kit according to claim 1, wherein said resilient carrier frame, said flexible shutter, and said integrated centripetal compression means are shaped and arranged such that contacting said centripetal compression means causes said resilient carrier frame to be compressed toward the folded position for removal or adjustment.

13. The kit according to claim 1, wherein said drive segments are curved to be convex inwardly toward said flexible shutter.

* * * * *